US005596992A

United States Patent [19]
Haaland et al.

[11] Patent Number: 5,596,992
[45] Date of Patent: Jan. 28, 1997

[54] MULTIVARIATE CLASSIFICATION OF INFRARED SPECTRA OF CELL AND TISSUE SAMPLES

[75] Inventors: David M. Haaland; Howland D. T. Jones; Edward V. Thomas, all of Albuquerque, N.M.

[73] Assignee: Sandia Corporation, Albuquerque, N.M.

[21] Appl. No.: 85,709

[22] Filed: Jun. 30, 1993

[51] Int. Cl.$^6$ .................................................. A61B 6/00
[52] U.S. Cl. .................... 128/664; 128/665; 128/633; 250/339.01; 250/339.11; 250/341.8
[58] Field of Search ..................... 128/664, 665, 128/633, 898; 356/320, 432; 250/339.01, 339.11, 340, 341.1, 341.2, 341.8

[56] References Cited

U.S. PATENT DOCUMENTS

| | | | |
|---|---|---|---|
| 4,213,036 | 7/1980 | Kopp et al. | 364/416 |
| 4,495,949 | 1/1985 | Stoller | 128/664 |
| 4,515,165 | 5/1985 | Carroll | 128/664 |
| 4,975,581 | 12/1990 | Robinson et al. | 128/633 |
| 4,981,138 | 1/1991 | Deckelbaum et al. | 128/665 |
| 5,036,853 | 8/1991 | Jeffcoat et al. | 128/665 X |
| 5,038,039 | 8/1991 | Wong et al. | |
| 5,137,030 | 1/1992 | Darougar | 128/757 |
| 5,168,039 | 12/1992 | Oong et al. | |
| 5,197,470 | 3/1993 | Helfer et al. | 128/664 |
| 5,261,410 | 11/1993 | Alfano et al. | 128/664 |
| 5,293,872 | 3/1994 | Alfano et al. | 128/665 X |
| 5,303,026 | 4/1994 | Strobl et al. | 128/665 X |
| 5,355,880 | 10/1994 | Thomas et al. | 128/633 |
| 5,379,764 | 1/1995 | Barnes et al. | 356/39 |
| 5,433,197 | 7/1995 | Stark | 128/633 |

OTHER PUBLICATIONS

Benedetti, E., et al., "Analytical Infrared Spectral Differences Between Human Normal and Leukaemic Cells (CLL)—I," Leukemia Research, vol. 8, (1984), pp. 484–489.

O'Leary, T. J., et al., "Infrared Microspectroscopy of Pathological Tissue," SPIE, vol. 1145, (1989), pp. 534–535.
O'Leary, T. J. et al., "Methods in Laboratory Investigation, Secondary Structure of Endocrine Amyloid: Infrared Spectroscopy of Medullary Carcinoma of the Thyroid," Laboratory Investigation, vol. 53, (1985), pp. 24–242.
Benedetti, E., et al., "FT–IR Analysis of Single Human Normal and Leukemic Lymphocytes," Mikrochim. Acta [Wien] vol. I, (1988), pp. 139–141.
Benedetti, E., et al., "A New Approach to the Study of Human Solid Tumor Cells by Means of FT–IR Microspectroscopy," Applied Spectroscopy, vol. 44, (1990), pp. 1276–1280.
Wong, P. T. T., et al., "Infrared Spectra of Microtome Sections of Human Colon Tissues," Applied Spectroscopy, vol. 44, (1990), pp. 1715–1718.
Rigas, B., et al., "Human Colorectal Cancers Display Abnormal Fourier–Transform Infrared Spectra," Proc. Natl. Acad. Sci. USA, vol. 87, (1990), pp. 8140–8144.
Wong, P. T. T., et al., "Pressure–Tuning Infrared Spectroscopy: Application to Cancer Research and Diagnosis," Canadian Chemical News, Nov./Dec., 1991, pp. 14–16.
Wong, P. T. T., et al., "Phosphodiester Stretching Bands in the Infrared Spectra of Human Tissues and Cultured Cells," Applied Spectroscopy, vol. 45, (1991), pp. 1563–1567.
Rigas, B., et al., "Human Colon Adenocarcinoma Cell Lines Display Infrared Spectroscopic Features of Malignant Colon Tissues," Cancer Research, vol. 52, (1992), pp. 84–88.

(List continued on next page.)

*Primary Examiner*—William E. Kamm
*Assistant Examiner*—Brian L. Casler
*Attorney, Agent, or Firm*—Gregory A. Cone

[57] ABSTRACT

Multivariate classification techniques are applied to spectra from cell and tissue samples irradiated with infrared radiation to determine if the samples are normal or abnormal (cancerous). Mid and near infrared radiation can be used for in vivo and in vitro classifications using at least different wavelengths.

23 Claims, 7 Drawing Sheets

OTHER PUBLICATIONS

Haaland, D. M., "Multivariate Calibration methods Applied to Quantitative FT–IR Analyses," in Practical Fourier Transform Infrared Spectroscopy, (J. R. Ferraro and K. Krishnan, eds.) Academic Press, New York, (1990), pp. 395–468.

Haaland, D. M., "Multivariate Calibration Methods applied to the Quantitative Analysis of Infrared Spectra," in Computer–Enhanced Analytical Spectroscopy, vol. 3, edited by P.C. Jurs, Plenum Press (1992), pp. 1–30.

Lindberg, W., et al., "Partial Least–Squares Method for Spectrofluorimetric Analysis of Mixtures of Humic Acid and Ligninsulfonate," Anal. Chem., vol. 55, (1983), pp. 643–648.

Haaland, D. M., et al., "Partial Least–Squares Methods for Spectral Analyses. 1. Relation to Other Quantitative Calibration Methods and the Extraction of Qualitative Information," Appl. Spectrosc., vol. 60, (1988), pp. 1202–1208.

Haaland, D. M., et al., "Partial Least–Squares Methods for Spectral Analyses. 2. Applications to Simulated and Glass Spectral Data," Appl. Spectrosc., vol. 60, (1988), pp. 1202–1208.

Fredericks, P. M., et al., "Materials Characterization Using Factor Analysis of FT–IR Spectra. Part 1: Results," Appl. Spectrosc., vol. 39, (1985), pp. 303–310.

Fredericks, P. M., et al., "Materials Characterization Using Factor Analysis of FT–IR Spectra. Part 2: Mathematical and Statistical Considerations," Appl. Spectrosc., vol. 39, (1985), pp. 311–316.

Thomas, E. V., et al., "Comparison and Multivariate Calibration Methods for Quantitative Spectral Analysis," Anal. Chem., vol. 62, (1990), pp. 1901–1099

MULTIVARIATE CLASSIFICATION OF INFRARED SPECTRA OF CELL AND TISSUE SAMPLES

BACKGROUND OF THE INVENTION

The government has rights to this invention pursuant to Contract No. DE-AC04-76DP00789 awarded by the Department of Energy.

This invention relates to a method and a system for classifying cells and tissue on the basis of their attenuation of infrared radiation at different wavelengths using multivariate analysis.

Classification of human or animal cell and tissue samples as normal, hyperplastic, dysplastic, or neoplastic (i.e., malignant or cancerous) is usually made by visual examination of stained samples under the microscope. The process of preparing the samples requires trained technicians; the examination and classification of samples demands licensed pathologists. Biopsied tissue obtained during surgery often must be evaluated rapidly to make decisions about more radical intervention. In addition for comparison in classification, the less invasive small-needle aspiration methods remove a small number of cells that may not represent the nature of surrounding cells and tissue structure. Thus, in many cases cell and tissue classifications must be made in difficult or ambiguous situations.

Recently, a number or research groups have shown that infrared (IR) spectroscopy of cells and tissue contain information helpful to pathologists in cell and tissue classification. Groups have shown that IR spectroscopy can help distinguish between normal and leukemic lymphocytes and lymphoblasts, between normal and neoplastic lung tissue, and between normal and cancerous colorectal cells. Medullary carcinoma of the thyroid has been detected with IR. Classification of normal, dysplastic, and cancerous cells of the cervix have been classified with the aid of infrared spectroscopy. The infrared spectra are sensitive to the differences in DNA and protein content of the cells, as well as to differences in protein structure and degree of methylation. Differences in the pressure response of the IR spectra of normal and neoplastic cells have been reported also. In all these works, univariate methods involving ratios of IR peak intensities or shifts in band positions are used in the spectral classification of the samples.

Changes in the IR spectrum of a sample may be subtle but are exhibited throughout many regions of the spectrum. We have discovered that the more powerful multivariate calibration or classification methods can increase significantly the sensitivity and reliability of IR spectral classification of the cell and tissue samples. We have used IR microspectroscopy to examine small numbers of cells in cytology and histopathology samples. In addition, the multivariate classification methods can be applied to near-infrared (NIR) spectra of tissue. Since NIR spectra consist of overtone and combinating vibrations based on the fundamental vibrations seen in the mid-IR, the NIR is expected to contain the same information which is useful in making the mid-IR classifications. The NIR will be more difficult to interpret visually but has the advantage of greater penetration depths. Thus, NIR might be used for non-invasive classification of tissue (e.g., to detect skin cancer) or for minimally invasive fiber-optic methods (e.g., to detect cervical or colorectal cancers, or other cancers accessible by fiber-optic sensors).

SUMMARY OF THE INVENTION

Cell and tissue samples respond to infrared radiation differently at various wavelengths depending upon a particular attribute or attributes of the sample. Analysis of IR attenuation ratios between normal and abnormal samples at individual wavelengths has provided a method of classifying such samples in the past. However, some normal/abnormal differences are so subtle as to be undetectable using such univariate analysis methods. We have now developed a method and apparatus for classifying cell and tissue samples as normal or abnormal using multivariate analysis which can accurately classify samples on the basis of these subtle responses. The initial development has been with IR data on cytology and histopathology samples with canine lyphoma as the test model. Accurate classifications can be made using infrared spectroscopy and multivariate calibration and classification methods of partial least squares (PLS), principal component regression (PCR), and linear discriminant analysis. These classifications can be made to distinguish normal, hyperplastic (i.e., normal but rapidly replicating cells), and neoplastic cells, or, more simply, normal and abnormal. Extensions of these methods to other neoplastic cells and tissues and to near-IR spectra for in-vivo determinations are also possible.

DETAILED DESCRIPTION OF THE INVENTION

Figure 1:
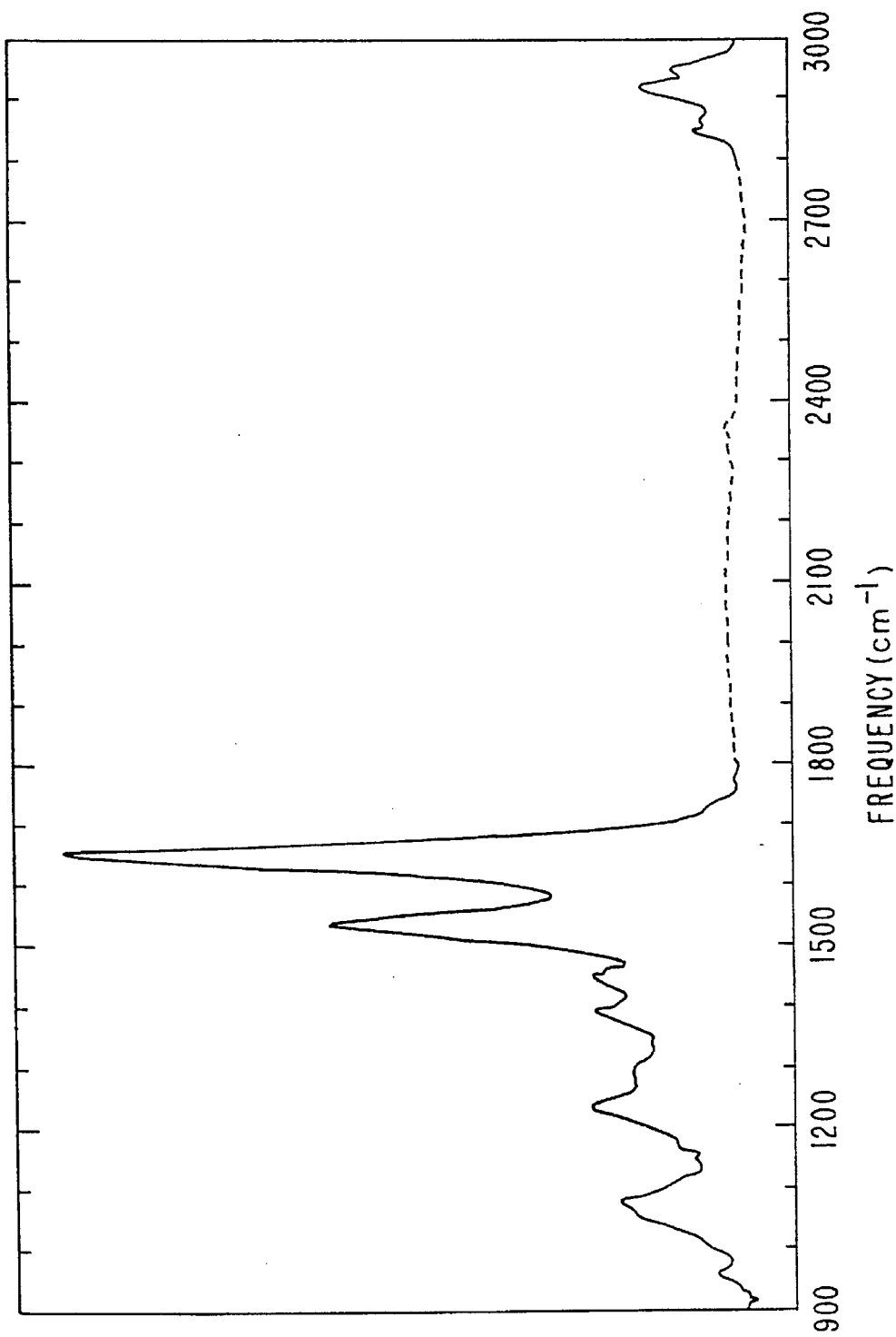
FIG. 1 is the mid-IR absorbance spectrum for a canine lyphoma sample.

It should be realized that techniques developed in conjunction with the specific experiments on canine lymphoma cells are not limited to such cells. The true scope of the invention will be found in the appended claims. Although the experiments used the relatively shallow penetrating mid-IR radiation (wavelengths of 25000 to 2500 nm or frequency from 400 to 4000 $cm^{-1}$), the technique can work also with the deeper penetrating near-IR radiation (2500 to 700 nm or 4000 to 14000 $cm^{-1}$). The possible cell and tissue classifications can include any of the abnormal states that can be discriminated from normal by their response to IR radiation.

Experiments/Technique

Normal, hyperplastic, and neoplastic lymph cells and tissues were obtained from dogs at the University of Purdue School of Veterinary Medicine. Cytology and histopathology samples were prepared by a variety of methods in several configurations to identify the optimal methods of sample preparation. Cytology samples were prepared by obtaining small-needle aspirations from lymph nodes or by making impressions smears of the biopsied lymph nodes. Samples were also prepared as a monocellular dispersion using a cytospin technique. These cell samples were placed on either $BaF_2$ infrared transparent windows for IR transmission measurements or on gold-coated slides for IR reflection measurements. The histopathology samples were obtained from thin (microtomed to 1 micrometer) sections of biopsied tissue in paraffin and placed on $BaF_2$ windows and gold-coated slides. Cytology samples were examined either with no further preparation or after staining separate samples with Wrights's stain or Diff-Quik stain. The histopathology samples were examined without further preparation, after fixing the samples in ethanol or after fixing and staining with H and E stain. The stained samples were classified by a pathologist at the University of Purdue. The pathologist classified samples as normal, hyperplastic (mild, moderate, or high hyperplasia) or neoplastic. Samples were obtained from a total of twenty-one dogs over a period of one year.

The samples were transported overnight to Sandia National Laboratories. Within 24 hours of preparation, they were examined using a Nicolet 800 Fourier transform infrared spectrometer coupled to a Spectrotech IR Plan redundant-apertured microscope. Spectra were collected at 4 $cm^{-1}$ resolution using a 100-μm aperture. A 100-μm diameter, liquid-nitrogen-cooled Hg-Cd-Te detector was used to obtain the IR signal from 700 to 4000 $cm^{-1}$. Samples on the $BaF_2$ windows were examined in transmission mode while samples on the gold-coated microscope slides were obtained in reflection. Signal-averaging of 512 scans was used for each sample spectrum. The visual microscope image isolated 100-μm diameter regions of homogeneous material. At least three spectra from different regions were obtained from each sample from each dog. Spectra were transferred to a 486-compatible PC or a DEC 8650 VAX computer for multivariate classification. Spectral data pre-processing included subtraction of the water vapor spectrum, linear baseline corrections over well-defined regions (2993–2835 and 1727–945 $cm^{-1}$), followed by a normalization of each spectral region to the maximum absorption band in that spectral region. A variety of spectral regions were examined separately or in combination to obtain optimal classification accuracy. Classifications were performed using partial least squares (PLS), principal component regression (PCR), and linear discriminant analysis although a variety of other multivariate analysis techniques (e.g. neural networks) could also have been applied to the data. When PLS and PCR were used for classification, the boundaries were determined by arbitrarily setting the value of normal cells as 0, hyperplastic as 0.5, and neoplastic as 1.0. In this manner, classifications could be based on the prediction closest to the value representing the three classes. Because the number of dogs was small, cross-validation techniques left out one sample (or one dog) at a time to improve sample use.

Linear discriminant analysis was performed by first compressing the spectral data to scores (principal components) using principal component-analysis (PCA) methods. The scores were then used in a linear-discriminant analysis using Mahalanobis distances as the criteria for classification.

Another advantage of multivariate methods is their great sensitivity to identifying outlier samples. Outlier samples are those that lie outside the range of the bulk of the calibration samples. The size and location of spectral residuals and/or scores from PLS, PCR, and PCA can be used to detect outliers in the calibration set and among future samples to be classified with IR spectroscopy. Outliers can be identified using spectral F ratios and statistical influence measures. This capability to detect outliers will assure the quality and reliability of the classifications.

Results and Discussion

FIG. 1 shows the absorbance infrared spectrum of a 100-μm area of a sample prepared on a $BaF_2$ window with the cytospin cell preparation technique. The dashed portion of the spectrum has low information content and was not included in any of the classification determinations. The baseline-corrected and normalized spectra in the $CH_2$ and $CH_3$ stretching region for normal, hyperplastic, and neoplastic samples are presented in FIG. 2. Spectra of the same samples in the finger-print region are shown in FIG. 3. The spectral region between 2800–3000 $cm^{-1}$ is the CH stretching region of saturated hydrocarbons representing primarily lipids. The two strong bands centered at 1650 and 1540 $cm^{-1}$ represent primarily the amide I and amide II bands of protein. The $CH_2$ bending vibration is found at 1467 $cm^{-1}$. The bands at 1450 and 1400 $cm^{-1}$ are the asymmetric and symmetric $CH_3$ bending vibrations, respectively. The amide III band occurs weakly at 1255 $cm^{-1}$. At 1240 and 1080 $cm^{-1}$ are the asymmetric and symmetric $PO_2$ stretching vibrations of nucleic acids. Shoulders on the low-energy side of the 1080 $cm^{-1}$ band at 1025 and 1047 $cm^{-1}$ have been assigned to the vibrational modes of glycogen or to DNA vibrations. A very weak band exists at 994 $cm^{-1}$. This band is generally observed only in the neoplastic sample. This has been assigned to an RNA vibration.

Figure 2:
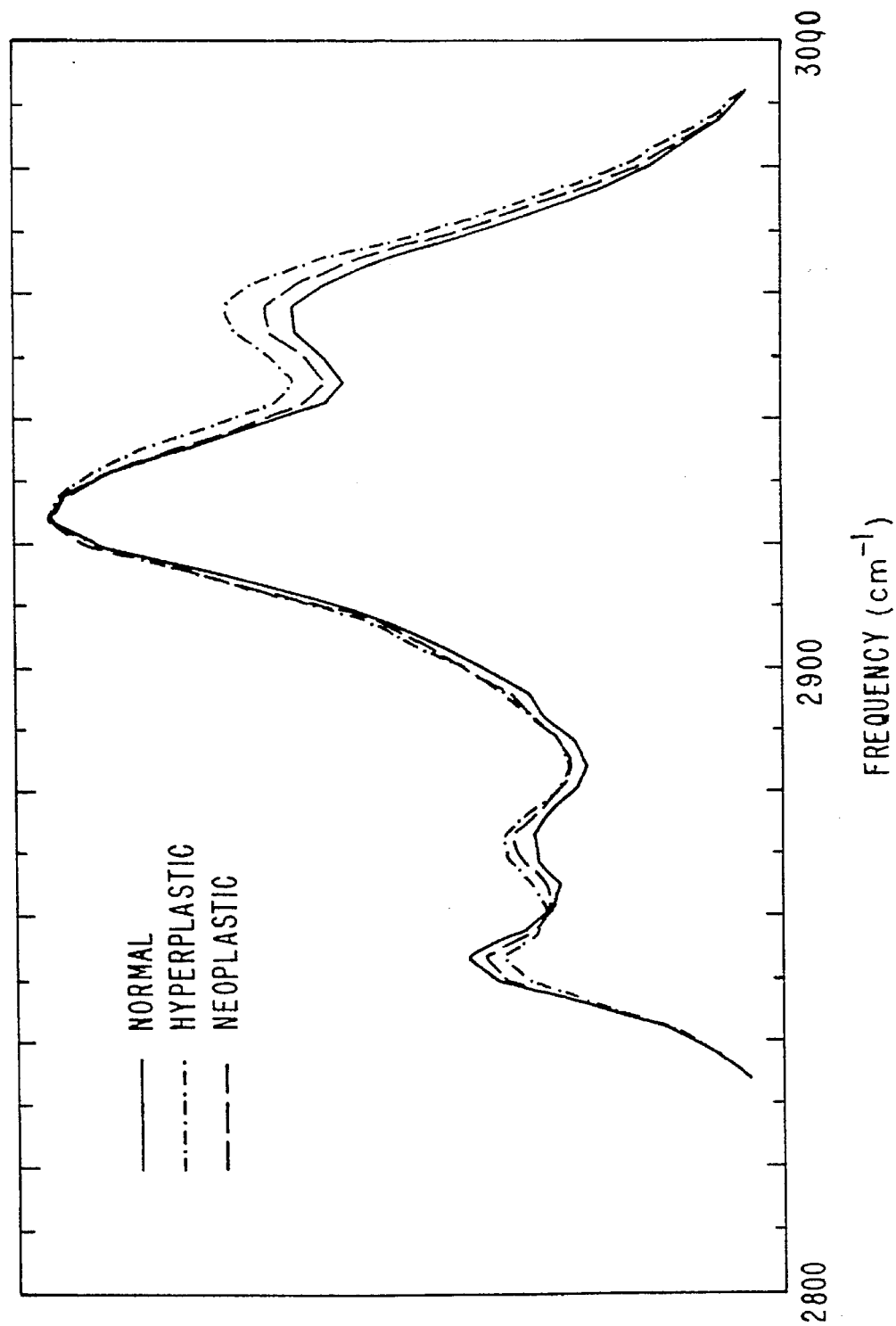
FIG. 2 is a of the spectrum of FIG. 1 showing responses for three different classes of the cells.
Figure 3:
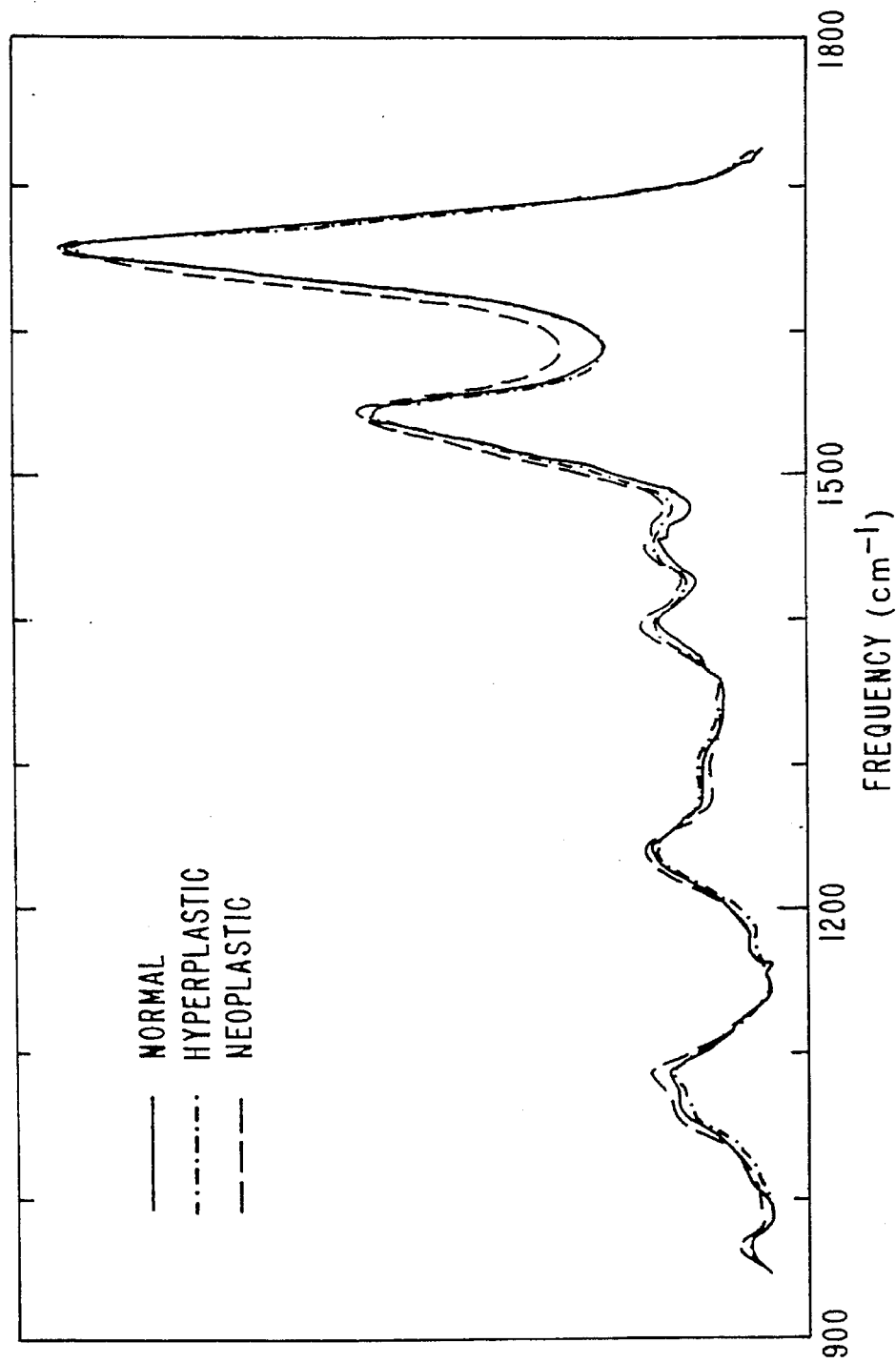
FIG. 3 is another portion of the spectrum showing responses for the three classes of the cells.

Although in FIGS. 2 and 3 differences are seen in the spectra presented, many of these differences are due to within-class sample-to-sample variations rather than to consistent differences between classes of samples.

The IR spectra of fixed and stained cytology and histopathology samples were studied also for classification determinations. However, the spectrum-to-spectrum within-sample variations were as great as any between-class variations for the samples with different classifications. These large within-sample variations rendered the spectral classifications by multivariate methods poor in their classification accuracy. The same large within-sample spectral variations were observed also for the unfixed histopathology samples and for the unfixed aspiration and impression smear cytology samples. Therefore, only the unfixed cytospun samples were observed to have small within-sample spectral variations due to the more uniform nature of these monocellular layer cytology preparations. This appears to be due to the very subtle differences in normal and abnormal canine lymphoma cells. For most other cancers, the differences between normal and abnormal are more distinct, and this monocellular layer cytology preparation will probably not be necessary when multivariate classification methods are employed for other cancers.

The unfixed cells are subject to changes with time. Making the first infrared measurements the day after the samples were collected caused concern that changes might have occurred during the initial twenty-four hours. Therefore, the spectra of several samples were followed as a function of time for five days. These studies indicated the spectra of the samples were relatively constant with time. Noticeable changes became apparent only after a period of five days. Thus, time-dependent changes during the first twenty-four hours of sample preparation do not appear to influence sample spectra that were consistently collected the day after preparation.

The observed spectral differences between normal, hyperplastic, and neoplastic cells are not nearly so great as are present in the literature of other tissue types. This may result from less differentiation between the lymph cells changing toward malignancy than found in the different tissue types discussed in the literature. In particular, consistent differences between normal and malignant tissues are observed visually in the infrared spectra presented in the literature. Few if any consistent spectral differences are observed visually between the normal and neoplastic lymph cells examined in this study.

Figure 4:
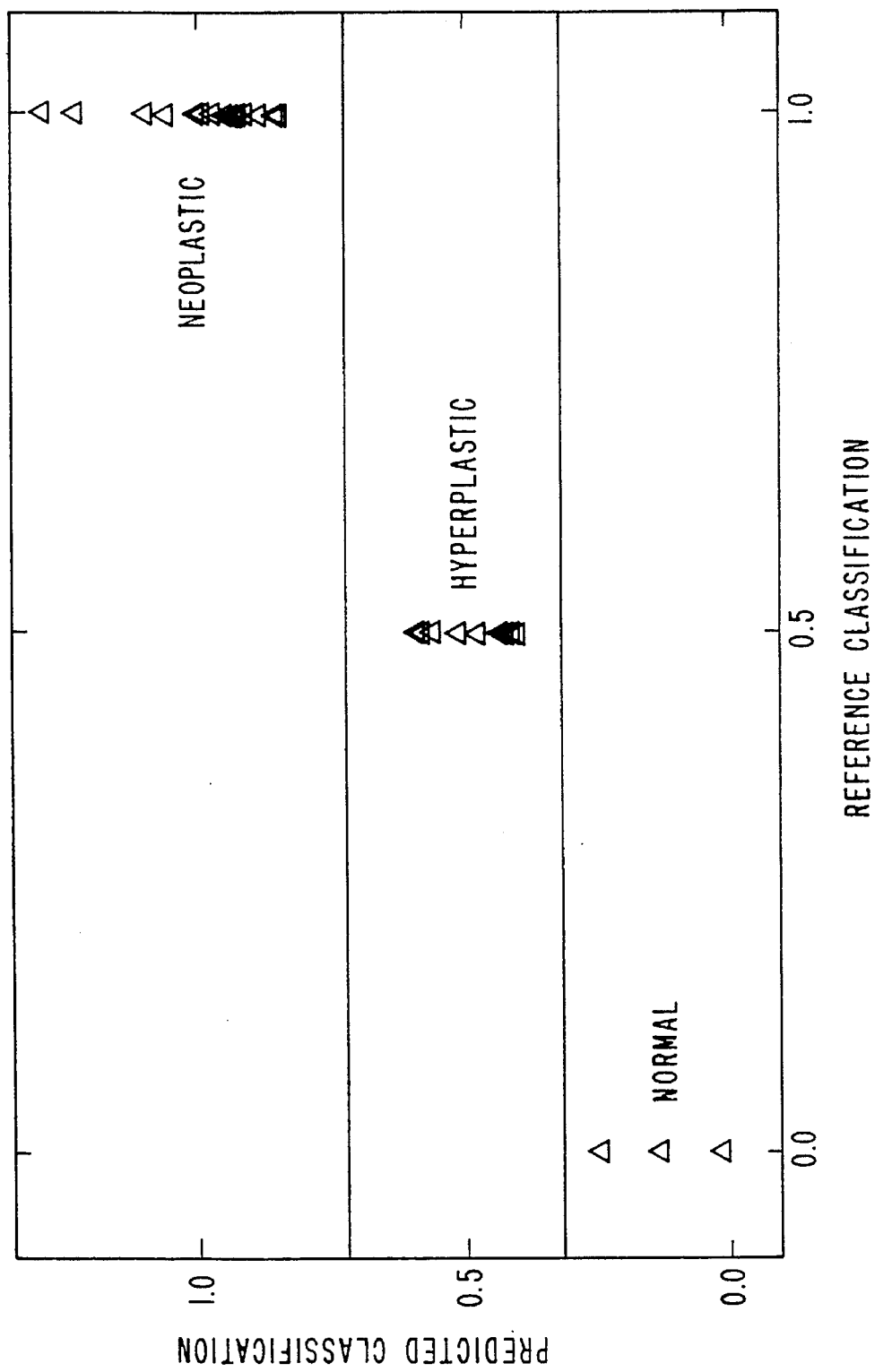
FIG. 4 is shows the results of a multivariate analysis of the mid-IR responses to classify the three classes of cells using the single-spectrum cross-validated partial least squares method.

Classification results using multivariate PLS methods are presented in FIG. 4. In this case, the classification values of 0, ½, and 1 are set arbitrarily to determine the classification model. The data in FIG. 4 are the result of cross-validated calibration omitting one spectrum at a time for each of the three replicate samples from the twelve dogs. As seen in FIG. 4, the three classes of cells are completely separated. This is indicated by the observation that all spectra of a given class fall between the dividing lines drawn between classes. Thus, spectra with a prediction below 0.32 are classified as normal; spectra predicted between 0.32 and 0.72 are hyperplastic; and spectra predicted above 0.72 will be classified as neoplastic.

Figure 5:
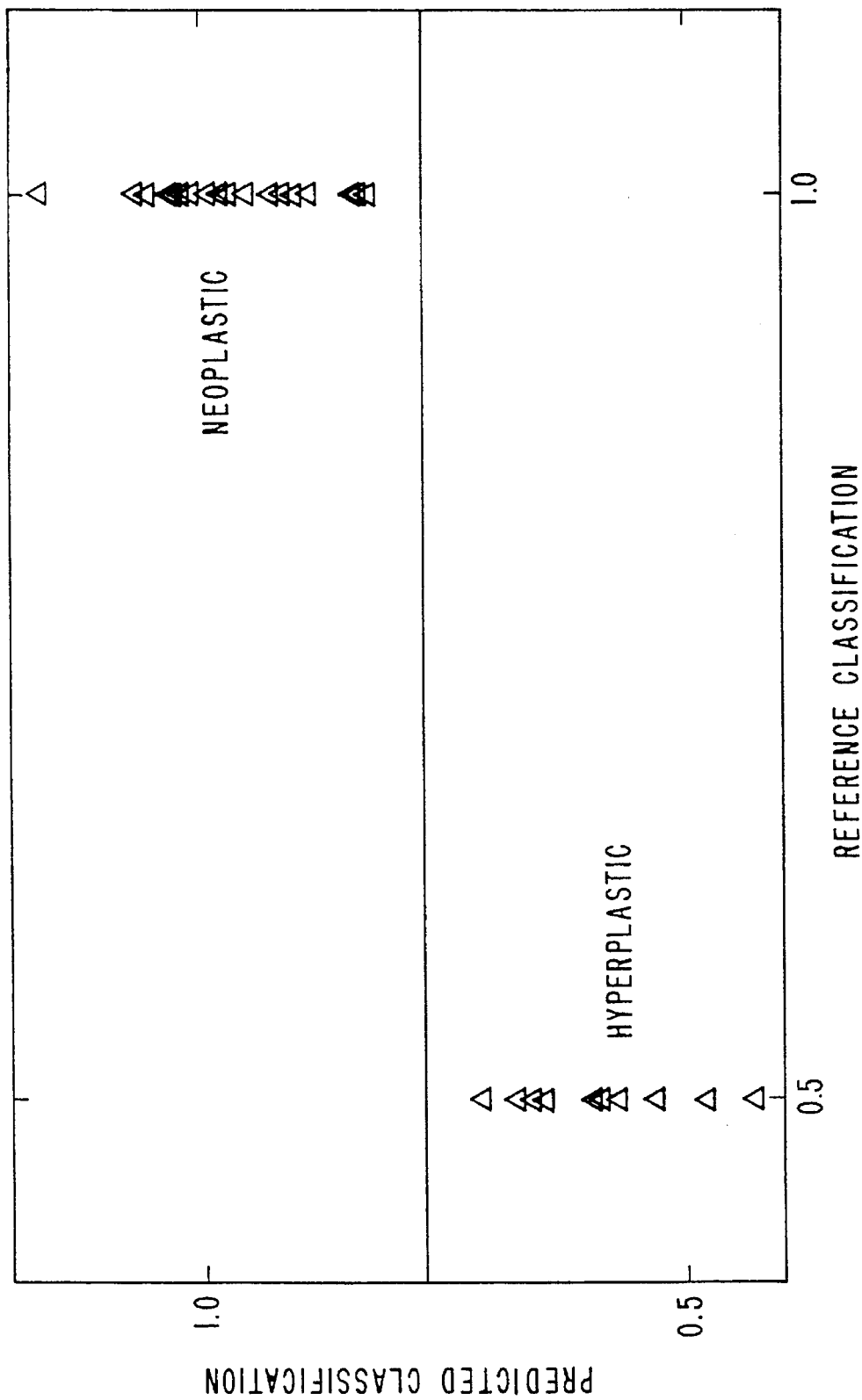
FIG. 5 is another multivariate analysis partial least squares identification of hyperplastic and neoplastic cells using cross validation methods leaving out a single dog's spectra during each cycle of the cross-validation procedure.

A more robust classification procedure would perform the PLS cross-validated classification rotation by separately omitting the set of spectra for each dog. Unfortunately, samples were available for only one dog classified as normal. Therefore, the cross-validation omission of data from one dog at a time would require extrapolation of neoplastic and hyperplastic cell spectra to normal cell spectra. Because this is not possible, a PLS-cross-validated classification leaving out one dog's spectrum at a time was employed, using only the samples that were pathologist-classified as hyperplastic or neoplastic. FIG. 5 shows the results of this cross-validated PLS classification. It demonstrates that the two types of cells that are more difficult to classify can be 100 percent classified using the more robust cross validation procedure of omitting all samples of one dog each time during cross-validation rotation. This classification allows mid-infrared microspectroscopy to credibly classify these two cell types when the multiple spectra from a given dog do not remain in the calibration model. PCR classifications yielded similar results as presented here for the PLS classifications.

Figure 6:
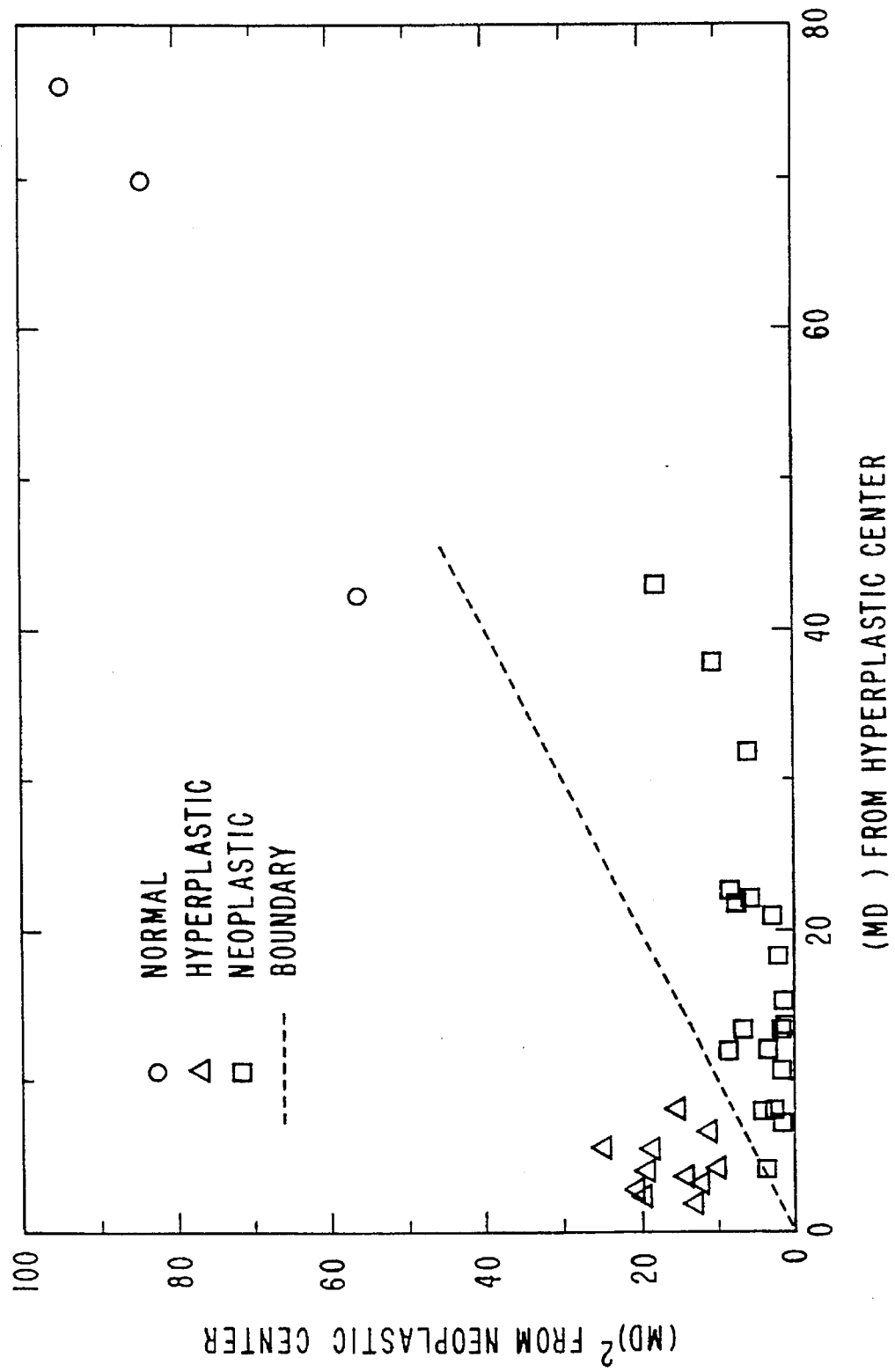
FIG. 6 illustrates classification using multivariate discriminate analysis with principal component discriminators to classify the three classes of cells.

Although classification by PLS has been demonstrated successful for canine lymphoma, discriminant analysis techniques are expected to achieve better classifications. Discriminant analysis will find the spectral descriptions that maximize the between-class distances relative to the within-class distances. Because the large number of spectral data points in the spectra make the discriminant analysis computationally intensive and less reliable, principal component analysis was first applied to the spectra to limit the discriminators to a small number of orthogonal variables (i.e., the principal components or scores). The number of principal components (h) important for discrimination are selected by cross-validation. The h-dimensional average scores and h×h dimensional covariance of scores are computed for each group. Then the average within-group covariance matrix of scores (S) is calculated. For the classification of the cells of an unknown sample, the h-dimensional score vector t is calculated from the measured spectrum and the eigenvectors determined in the initial calibration of spectra from cells of known classification. The Mahalanobis distances from t to the average score for each group d(1), d(2), and d(3) are computed. A new sample with unknown class is classified as belonging to the group to which it is nearest in terms of Mahalanobis distance. Best separation and classifications between groups were obtained for the canine lymphoma samples by using only five principal components. This method produced 100 percent classification of the three classes of cells. FIG. 6 shows this five-factor classification, which demonstrates that the three classes are completely discriminated using Mahalanobis distances based upon the five-principal-component model.

Additional embodiments of this invention are described below. Mid-infrared spectroscopy using mid-infrared fiber-optic probes could be used for invivo detection of cancers on the surfaces of tissues. These might include the detection of skin, cervical, uterine, colorectal, mouth, throat, esophageal, or stomach cancers. In addition, depending on the wavelength range used, the depth of penetration of near-infrared radiation in tissue could be a fraction of a millimeter to more than 10 millimeters. Thus, cancers that are deeper than surface level might be detected with a near-infrared in vivo fiber-optic probe. Detection of the cancers listed above would be possible, as well as of prostate and other cancers that could be sampled within a centimeter of the fiber-optic probe. Fiber-optic probes in the mid- or near-infrared spectral ranges could be used also during biopsies to achieve rapid classifications of tissue and cells during the surgical procedure. When using fiber optic probes, bifurcated fiber optics would be used to both bring the source IR radiation to the cells or tissue to be classified as well as to collect the reflected IR radiation to be analyzed with the appropriate frequency separations spectrometer device. The frequency-separated IR radiation collected would then be made to impinge on the IR detector.

Figure 7:
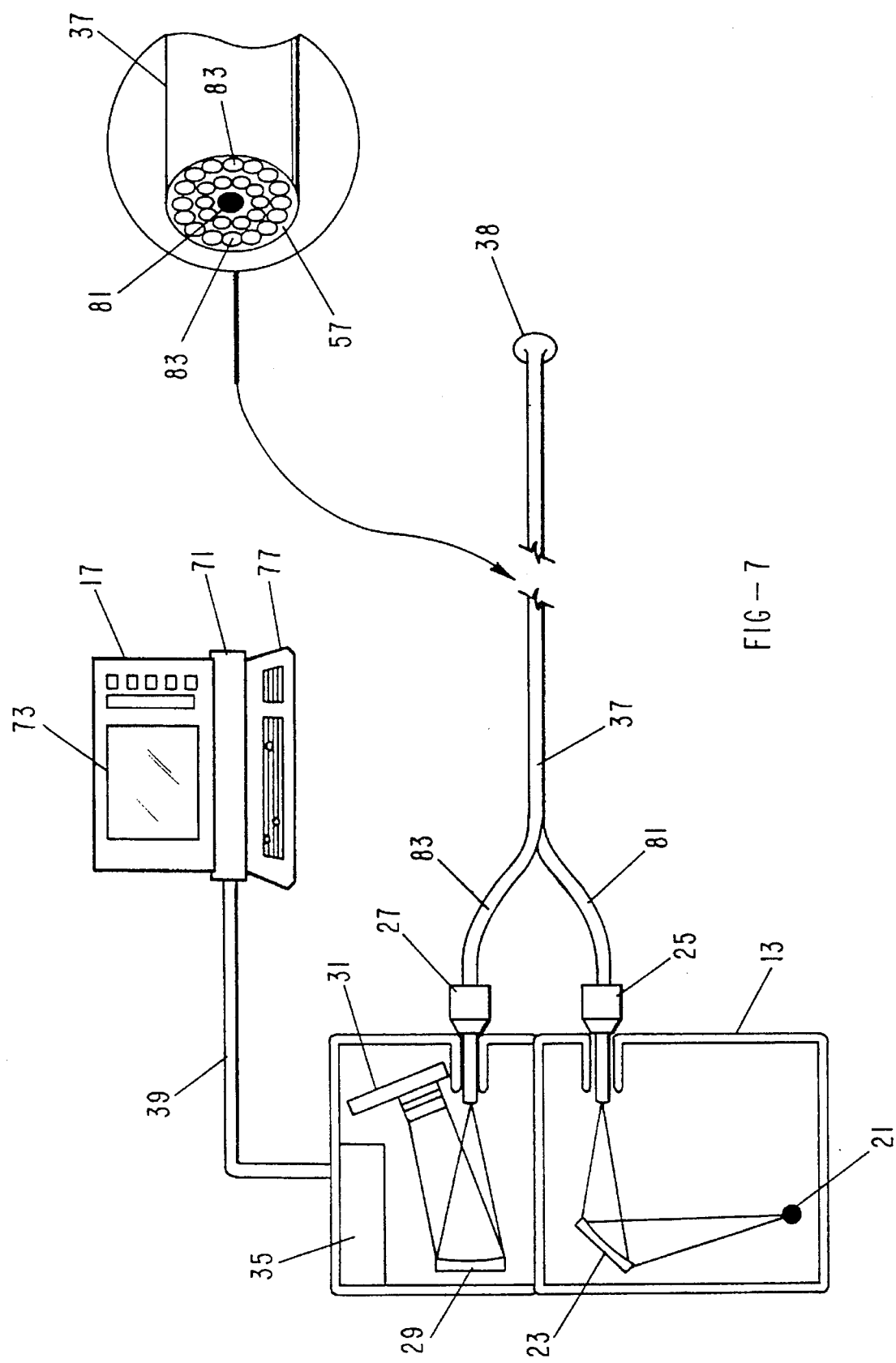
FIG. 7 is a schematic diagram of an apparatus useful in conducting the classifications contemplated by this invention.

FIG. 7 is a representation of one possible apparatus to accomplish the in vivo classifications contemplated by this invention. The apparatus has three main sub-components: the fiber optic cable bundle 37, the IR spectrometer 13, and the computer 17. The spectrometer 13 includes a IR light source 21, a concave focusing mirror 23, a fiber optic housing 25, a second fiber optic housing 27, a wavelength dispersion device (i.e. a grating) 29, an array detector 31, and spectrometer electronics 35 to convert the output of the array detector 31 into a signal usable by a computer. The spectrometer is connected to the sensing head unit 38 of the fiber optic bundle 37 and to a computer 17. The computer 17 includes a microprocessor and associated electronics 71, a video monitor 73, and a keyboard 77 and is connected to the spectrometer 13 via a cable 39. The fiber optic bundle 37 includes the illuminating fiber optic cable 81 at its center and the collecting fiber optic strands 83 surrounding the illuminating cable 81 as shown. The collecting strands 83 receive the IR radiation reflecting back from the illuminated region for transmission back to the spectrometer 13. The cable 37 has an outer covering 57. At the end of the cable would be located a probe 38 useful for the particular application. This could be an IR-transparent endoscope for colo-rectal, cervical, uterine, etc. cancer testing or a more conventional surface probe for skin cancer investigations. The signals received from the collecting optics 83 are separated into the various frequencies or wavelengths by the grating 29 and then sensed and converted into intensity levels at the various frequencies or wavelengths. The intensity variations are then conducted to the computer 17 for storage, further processing, and classification determination.

Attenuated total reflection (ATR) methods also could be employed in the mid-infrared to potentially increase sensitivity of cytology, histopathology, in in-vivo surface sampling. An infrared microscope coupled with an ATR objective could be used for cytology and histopathology samples. Harrick's nano-ATR sampling could be used also for small-spot sampling of cytology samples, histopathology samples, and in-vivo monitoring of suspected skin cancers. Regular ATR or Axiom's Tunnel Cell sampling would be possible for easily-accessed tissue, such as skin, mouth, and throat tissue.

As the cited literature indicates, cancers other than canine lymphoma may be more differentiated. Therefore, in vitro cell and tissue samples may be classified possibly based on the more standard preparations using fixed and/or stained cytology and histopathology samples. This would allow more standard sample preparation procedures used in the spectral classification of cells and tissues.

The methods described above might serve as a rapid screening tool for pap smears also. Finally, these methods might be used for early detection of cancers or to monitor the progress of cancer treatments, such as chemo- and radiation therapies.

We claim:

1. A method of classifying a cell or tissue sample comprising:
   generating a plurality of different wavelengths of infrared light;
   irradiating the sample with the plurality of different wavelengths so that there is differential intensity attenuation caused by variations between different classes of the sample as a function of the different wavelengths;
   measuring such intensity attenuations to obtain intensity information at at least three different wavelengths; and
   classifying the sample as one of two or more cell or tissue types from the measured intensity attenuations by using a multivariate classification model.

2. The method of claim 1 wherein the infrared light is in the mid-infrared range of wavelengths.

3. The method of claim 1 wherein the infrared light is in the near-infrared range of wavelengths.

4. The method of claim 1 wherein the sample is classified as normal or abnormal.

5. The method of claim 1 wherein the sample is classified as normal, hyperplastic, dysplastic or neoplastic.

6. The method of claim 1 wherein the irradiating of the sample is done in vitro.

7. The method of claim 6 wherein the irradiating of the sample further includes the step of presenting the sample as a monocellular layer.

8. The method of claim 7 wherein the irradiating of the sample further includes the step of presenting the sample by a cytospin cell preparation technique.

9. The method of claim 1 wherein the irradiating of the sample is done in vivo.

10. The method of claim 1 wherein the classifying of the samples includes at least one spectral data pre-processing step.

11. The method of claim 10 wherein the pre-processing includes at least one of the steps of selecting wavelengths, subtracting a water vapor spectrum, correcting for a linear baseline, and normalizing a spectral region surrounding the different wavelengths, used for classification to one maximum absorption band in that spectral region.

12. The method of claim 11 further including the step of selecting the maximum absorption band in that spectral region as the one maximum absorption band.

13. The method of claim 1 wherein the multivariate classification is done by a partial least squares technique.

14. The method of claim 1 wherein the multivariate classification is done by a principal component regression technique.

15. The method of claim 1 wherein the multivariate classification is done by a linear discriminant analysis technique.

16. The method of claim 15 wherein the linear discriminant analysis is preceded by principal component analysis step limiting the number of discriminant variables.

17. A method of classifying a cell or tissue sample comprising:
   generating a plurality of different wavelengths of mid-infrared light;
   irradiating the sample with the plurality of different wavelengths so that there is differential intensity attenuation caused by variations between different classes of the sample as a function of the different wavelengths;
   measuring such intensity attenuations to obtain intensity information at at least three different wavelengths;
   generating at least one multivariate classification model, said model classifying the different classes of the sample as a function of their different attenuation characteristics at the at least three different wavelengths in relation to a reference classification;
   calculating the classification of the sample from the measured intensity attenuations by using multivariate classification of the intensity attenuations at the at least three different wavelengths based on the classification model; and classifying the sample as one of two or more cell or tissue types from the measured intensity attenuations by using said multivariate classification model.

18. The method of claim 17 further including classifying said sample in vitro.

19. The method of claim 17 further including classifying said sample in vivo.

20. A system for classifying cell or tissue samples comprising:
   means for generating a plurality of different wavelengths of infrared light;
   means for directing at least a portion of the infrared light into the samples;
   means for collecting at least a portion of the infrared light after it has interacted with the samples;
   means for measuring an intensity of the collected infrared light at at least three different wavelengths;
   means, coupled to the measuring means, for storing the measured intensities as a function of the wavelength;
   means for storing at least one multivariate classification model which contains data indicative of a correct classification of known cell or tissue samples; and
   processor means coupled to the means for storing the measured intensities and the means for storing the model, the processor means serving as means for calculating the classification of the cell or tissue samples as one of two or more cell or tissue by use of the multivariate classification model and the measured intensities.

21. The system of claim 20 wherein the means to direct the light and the means to collect the light comprise an endoscope.

22. The system of claim 20 further includes means to determine outliers.

23. The method of claim 1 wherein the step of classifying the sample is performed by a multivariate algorithm using the measured intensity information and at least one multivariate classification model which is a function of conventionally determined cell or tissue sample classes from a set of reference samples and a set of spectral intensities as a function of wavelength obtained from irradiating the set of reference samples with infrared light.

* * * * *